(12) United States Patent
Loffler et al.

(10) Patent No.: US 6,196,964 B1
(45) Date of Patent: Mar. 6, 2001

(54) COMBINATION OF A CAPSULE FOR BRACHYTHERAPY AND A GUIDEWIRE

(75) Inventors: Edgar German Loffler, Kleve (DE); Arie Luite Visscher, Driebergen (NL)

(73) Assignee: Delft Instruments Intellectual Property B.V., Delft (NL)

( * ) Notice: Subject to any disclaimer, the term of this patent is extended or adjusted under 35 U.S.C. 154(b) by 0 days.

(21) Appl. No.: 09/214,310

(22) PCT Filed: Jul. 4, 1997

(86) PCT No.: PCT/NL97/00385

§ 371 Date: Mar. 3, 1999

§ 102(e) Date: Mar. 3, 1999

(87) PCT Pub. No.: WO98/01184

PCT Pub. Date: Jan. 15, 1998

(30) Foreign Application Priority Data

Jul. 5, 1996 (NL) .................................... 1003528

(51) Int. Cl.[7] ............................. A61M 36/00; A61N 5/00
(52) U.S. Cl. .................................................. 600/7
(58) Field of Search ................... 600/1, 2, 3, 4, 600/5, 6, 7

(56) References Cited

U.S. PATENT DOCUMENTS

| 4,861,520 | 8/1989 | van't Hooft et al. . | |
| 5,141,487 | * 8/1992 | Liprie | 600/7 |
| 5,282,781 | 2/1994 | Liprie . | |
| 5,688,220 | * 11/1997 | Verin et al. | 600/1 |

FOREIGN PATENT DOCUMENTS

| 0 466 681 | 1/1992 | (EP) . |
| 92/00776 | 1/1992 | (WO) . |
| 94/23789 | 10/1994 | (WO) . |
| WO9425106 | 11/1994 | (WO) . |
| WO9640352 | 12/1996 | (WO) . |

* cited by examiner

Primary Examiner—Max Hindenburg
Assistant Examiner—Brian Szmal
(74) Attorney, Agent, or Firm—Birch, Stewart, Kolasch & Birch, LLP

(57) ABSTRACT

A combination of a capsule for incorporating a radioactive source to be applied in brachytherapy and a guidewire, in which the capsule is attached to the guidewire via an adapter, and the adapter comprises a cable or thread with a flexibility greater than that of the guidewire

5 Claims, 1 Drawing Sheet

COMBINATION OF A CAPSULE FOR BRACHYTHERAPY AND A GUIDEWIRE

FIELD OF THE INVENTION

The invention relates to a combination of a capsule for incorporating a radioactive source to be applied in brachytherapy and a guidewire.

DESCRIPTION OF THE BACKGROUND ART

Such a combination is known in practice and described, for instance, in U.S. Pat. No. 4,861,520, which is herewith incorporated by reference.

For local radioactive radiation treatment of a specific internal area of the human body, such as a tumor, or a wall section of a blood vessel, it is possible, as described in U.S. Pat. No. 4,861,520, to deliver a capsule with a radioactive source, via a hollow needle, a flexible tube or a catheter or the like, to the area to be treated. For this purpose, normally the so-called "after loading" technique is employed. First, the catheter, or the like, is placed in the body and then the capsule attached to the distal end of a guidewire is delivered with the help of a remotely controlled device to the treatment area.

The combination of the capsule and guidewire should, on the one hand, have a high degree of flexibility to be able to follow the curves of a catheter or the like, and on the other, a certain rigidity, so that the capsule can be pushed through a catheter toward its distal end with the help of the guidewire. For the application in endovascular brachytherapy, a catheter normally has an inside diameter on the order of 1.5 mm or less. The length of a capsule depends on the desired strength of the radioactive source placed in the capsule, but should be on the order of several times the diameter, for instance in the range of 5 to 7 mm. The capsule itself and its connection with the guidewire are not flexible, so that the front part of the combination of guidewire and capsule has a relatively low degree of flexibility. Thus there is a certain probability that the capsule cannot pass the curves in a catheter with a strong curvature or only passes with difficulty.

SUMMARY OF THE INVENTION

The invention is intended to reduce the outlined problem and, in general, to make available a combination of a capsule and a guidewire that can be applied in a reliable way in a large number of situations, including situations in which strongly curved courses are to be passed in the catheter or the like.

For this purpose, a combination of the above-mentioned type is characterized in that the capsule is attached to the guidewire via an adapter, in which the adapter comprises a cable or a thread with a flexibility greater than the flexibility of the guidewire.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will be described in more detail in the following with reference to the attached drawing of some embodiments.

DETAILED DESCRIPTION OF THE PREFERRED EMBODIMENT

Figure 1:
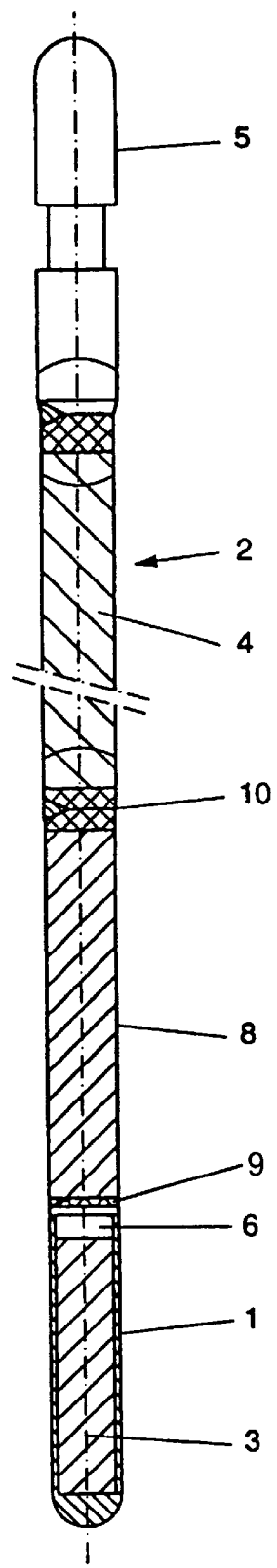
FIG. 1 shows a diagram of a first embodiment of a combination according to the invention.

FIG. 1 shows a diagram of a first embodiment of a combination of a capsule 1 for brachytherapy and a guidewire 2. The capsule comprises one or more radioactive sources, for example a small Iridium rod 3, as shown in the drawing. The guidewire 2 comprises in a known manner a thin cable 4, which at its proximal end is provided with a coupling element 5 in order to manipulate the guidewire with the capsule. Usually, the cable 4 has essentially the same diameter as the capsule 1. The cable 4 is both supple and solid, so that on the one hand, it can be used to push the capsule through a catheter or the like, and on the other is able to follow a curved path in a catheter or the like. The cable has a diameter that may not be much smaller than the inside diameter of the catheter or the like, since otherwise there is a risk that the cable will rest in a meandering way in the catheter or the like, whereby the position of the capsule with regard to the proximal end of the catheter or the like no longer is clearly defined.

In the known combinations, the capsule is attached to the distal end of the cable via a connecting piece 6, e.g., through a laser weld. As a consequence, the front end of the guidewire forms a rather rigid entity thereby restricting the ability of the capsule to follow strongly bent curves in the catheter or the like. According to the invention, the flexibility of the front end of the combination of the capsule and guidewire is therefore improved, since the capsule with its connecting piece is not directly attached to the distal end of the cable 4, but rather through a thread or cable-shaped adapter having a higher degree of flexibility than cable 4. This desired higher degree of flexibility can be obtained by applying a thread or cable of a more flexible material and/or structure imparting a more flexible thread or cable. The adapter may thus consist of, for example, a short cable section with a larger number of thin filaments than the guidewire itself, although with the same diameter as the guidewire. Such an embodiment is shown in FIG. 1. The adapter is indicated with 8 in FIG. 1 and is attached to one end with, for instance, a laser weld 9 and axially with its end surface against the capsule 3 or a connecting piece 6 placed on the capsule, whereby the longitudinal center lines essentially are lying in each other's extensions. The other end is attached in a similar manner, e.g., through a laser weld 10 with its head surface at the distal end of the guidewire.

Figure 2:
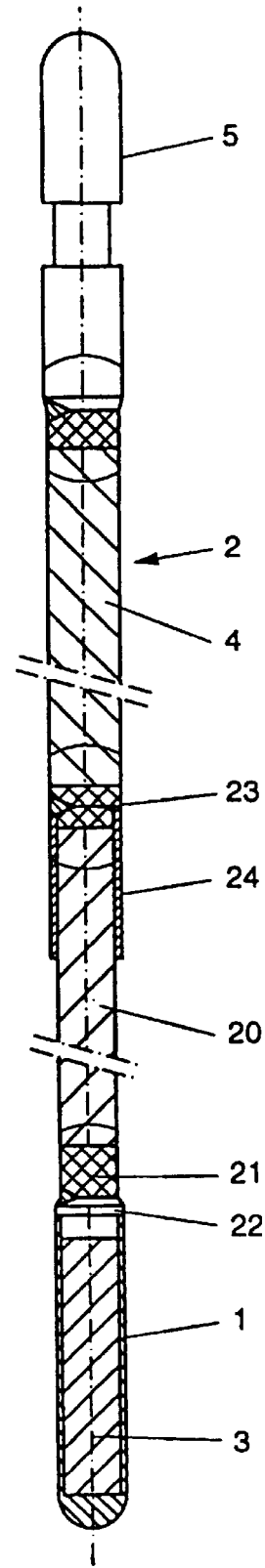
FIG. 2 shows a diagram of a second embodiment of the combination according to the invention.

According to a preferred embodiment of the invention, the greater flexibility of the distal end of the combination of guidewire and capsule is obtained through applying an adapter with smaller diameter than the guidewire itself and the capsule. A thread or cable with a smaller diameter automatically means a greater flexibility than a similar thread or cable with a greater diameter. This effect, of course, can be enhanced by applying a more supple material and/or a construction and/or combination imparting a more flexible thread or cable. Thus, for example the adapter can be built up from a larger number of and thinner filaments than the guidewire itself. Such an embodiment is shown in FIG. 2. The adapter with reduced diameter is indicated with 20 and is connected with its head surface at one end, for instance through a laser weld 21, with a suitable connecting piece 22 that in turn is connected with the capsule 1. At the other end, the adapter 20 is attached, for instance, through a laser welding 23 with its head surface against the distal end of the guidewire. At both ends, the longitudinal center line of the adapter again essentially coincides with the centerline of the guidewire or the connecting piece, respectively, and the capsule. In the shown example, a short casing 24 is also applied, which is placed over the end of the adapter attached to the guidewire and welded to the guidewire. The inside diameter of the casing is such that the casing fits snugly around the adapter, whereas the outside diameter of the casing is essentially equal to the diameter of the guidewire 2.

Applying such a casing prevents, even after a great number of bendings, that the outermost filaments of the adapter come loose from the weld and jut out. In a practical embodiment, the guidewire may consist of, for instance, a 0.9 mm diameter cable constructed of 1×19 filaments, whereas the more flexible adapter may consist of a 0.72 mm diameter cable constructed of 7×7 filaments. The casing may thus have a length of, for instance, ±2 mm. In a practical embodiment, the adapter may have a length of, for instance, 10–15 cm, while the total length of the combination may be about 2 m.

It should be noted that according to the abovementioned, various modifications may be obvious to a person skilled in the art. This naturally applies to the dimensions that are solely provided as examples and, furthermore, for the structure of the cables and the choice of materials. Such modifications are deemed to be within the scope of the invention.

What is claimed is:

1. A combination of a capsule for incorporating a radioactive source to be applied in brachytherapy and a guidewire, the combination comprising a capsule, and adapter and a guidewire, the capsule being fixedly attached to the guidewire by the adapter, the adapter includes a cable or a thread with a flexibility greater than that of the guidewire.

2. The combination according to claim 1, wherein the adapter has a smaller diameter than the guidewire.

3. The combination according to claim 1, wherein the adapter and the guidewire are welded at their front edges to one another, longitudinal center lines of the adapter and guidewire substantially coincide.

4. The combination according to claim 1, further comprising a casing around the adapter at an end of the adapter connected to the guidewire, the casing having a head surface welded to the guidewire.

5. The combination according to claim 4, wherein the casing and the guidewire have substantially the same outside diameter.

* * * * *